(12) United States Patent
Meier

(10) Patent No.: US 9,057,015 B2
(45) Date of Patent: Jun. 16, 2015

(54) FLUORESCENT DYES FOR PAPER DYEING

(75) Inventor: Helmut-Martin Meier, Ratingen (DE)

(73) Assignee: Kemira Germany GmbH, Leverkusen (DE)

(*) Notice: Subject to any disclaimer, the term of this patent is extended or adjusted under 35 U.S.C. 154(b) by 0 days.

(21) Appl. No.: 13/701,708

(22) PCT Filed: Jun. 15, 2011

(86) PCT No.: PCT/EP2011/059955
§ 371 (c)(1),
(2), (4) Date: Dec. 3, 2012

(87) PCT Pub. No.: WO2012/000794
PCT Pub. Date: Jan. 5, 2012

(65) Prior Publication Data
US 2013/0105099 A1 May 2, 2013

(30) Foreign Application Priority Data
Jun. 28, 2010 (EP) .................................... 10167519

(51) Int. Cl.
| | | |
|---|---|---|
| *C09K 11/06* | (2006.01) | |
| *D21H 21/30* | (2006.01) | |
| *D21H 21/40* | (2006.01) | |
| *C07F 5/02* | (2006.01) | |
| *C09B 57/00* | (2006.01) | |
| *C09B 67/20* | (2006.01) | |
| *C09B 67/46* | (2006.01) | |
| *D21H 21/28* | (2006.01) | |
| *D21H 21/08* | (2006.01) | |
| *D21H 23/56* | (2006.01) | |

(52) U.S. Cl.
CPC ................ *C09K 11/06* (2013.01); *D21H 21/30* (2013.01); *D21H 21/40* (2013.01); *C07F 5/022* (2013.01); *C09B 57/00* (2013.01); *C09B 67/0066* (2013.01); *C09B 67/0089* (2013.01); *D21H 21/08* (2013.01); *D21H 21/28* (2013.01); *D21H 23/56* (2013.01)

(58) Field of Classification Search
CPC ............................... D21H 21/30; D21H 21/40
USPC ........................ 162/72, 158, 162; 252/301.16
See application file for complete search history.

(56) References Cited

U.S. PATENT DOCUMENTS

| 4,136,229 A | 1/1979 | Godet et al. |
|---|---|---|
| 2002/0132737 A1 | 9/2002 | Meier et al. |
| 2009/0084510 A1* | 4/2009 | Perry et al. ...................... 162/49 |
| 2009/0176313 A1* | 7/2009 | Suzuki et al. ................. 436/172 |
| 2010/0231125 A1* | 9/2010 | Li et al. ......................... 313/504 |

FOREIGN PATENT DOCUMENTS

| JP | 54064113 A | 5/1979 |
|---|---|---|
| JP | H06093600 A | 4/1994 |
| JP | 2002114845 A | 4/2002 |

OTHER PUBLICATIONS

Baum, Thin film printed electronics on paper substrates, 2007, Tappi Nanotechnology Conference.*
Ophardt Charles, Virtual Chembook: Polarity of Organic Compounds, 2003, Elmhurst College.*
The International Preliminary Report on Patentability dated Jan. 10, 2013.
The International Search Report and Written Opinion dated Jul. 22, 2011.
Chen, et al., "4, 4-Difluoro-4-Bora-3A, 4A-Diaza-S-Indacen E (Bodipy) Dyes Modified for Extended Conjugation and Restricted Bond Rotations," Journal of Organic Chemistry, American Chemical Society, vol. 65, Jan. 1, 2000, pp. 2900-2906, XP000960871.
Umezawa, et al., "Bright, Color-Tunable Fluorescent Dyes in the Vis/NIR Region," Chem. Eur. J., vol. 15, 2009, pp. 1096-1106, XP002602607.

* cited by examiner

*Primary Examiner* — Anthony Calandra
(74) *Attorney, Agent, or Firm* — Thomas Horstemeyer LLP

(57) ABSTRACT

The present invention relates to an aqueous preparation comprising a fluorescent dyestuff of a specific formula, water, and optionally a dispersing agent, and the use of the aqueous preparation for dyeing cellulose- or polyamide-containing materials.

11 Claims, No Drawings

FLUORESCENT DYES FOR PAPER DYEING

CROSS REFERENCE TO RELATED APPLICATION

This application is the 35 U.S.C. §371 national stage of PCT application entitled "FLUORESCENT DYES FOR PAPER DYEING," having serial number PCT/EP2011/059955,filed on 15 Jun. 2011, which claims priority to European Application No. 10167519.7, filing date Jun. 28, 2010, both of which are incorporated by reference in there entireties.

DETAILED DESCRIPTION

The present invention relates to an aqueous preparation of a fluorescent dye and its use in dyeing cellulose- or polyamide-containing materials, in particular paper. The dyestuff contains the structural element of a boron dipyrromethene skeleton as shown below.

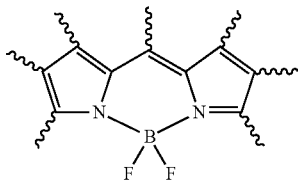

EP 2 022 794 A1 and US 2008/0311041 A1 disclose molecules with such a boron dipyrromethene skeleton as fluorescent compounds and labeling agents in biological samples. Further, such fluorescent dyes are known from J. Am. Chem. Soc. 2008, 130, 1550-1551, and Chem. Eur. J. 2009, 15, 1096-1106. The latter article also discloses for two specific dyes an aqueous solution thereof with DMSO.

It has now been found that aqueous preparations can be prepared from specific fluorescent compounds with boron dipyrromethene skeleton and used for dyeing, in particular as paper dyes.

Accordingly, the present invention relates to an aqueous preparation containing a compound of formula (1)

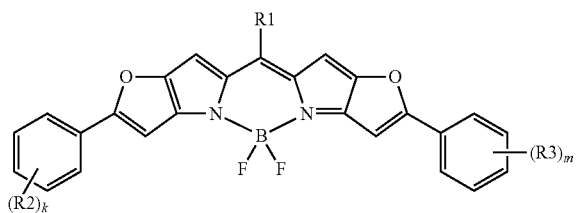

(1)

wherein
R1 represents hydrogen, CN, CF$_3$, Br, Cl, I; optionally substituted aryl; or optionally substituted alkyl;
R2 and R3, independently of each other, represent hydrogen, C$_{1-5}$-alkyl, C$_{1-5}$-alkoxyl, optionally substituted aryl, optionally substituted phenyl, p-C$_{1-5}$-alkoxyphenyl, di(C$_{1-5}$-alkyl)amino group, or —SO$_3$M; wherein M is a cation, preferably hydrogen, alkaline metal, earth alkaline metal, ammonium, or mono-, di-, tri- or tetra-substituted ammonium, in particular mono-C$_{1-5}$-alkyl-, di-C$_{1-5}$-alkyl-, tri-C$_{1-5}$-alkyl-, tetra-C$_{1-5}$-alkylammonium, mono-C$_{1-5}$-hydroxyalkyl-, di-C$_{1-5}$-hydroxyalkyl-, tri-C$_{1-5}$-hydroxyalkyl-, tetra-C$_{1-5}$-hydroxyalkylammonium, or benzyl-tri-C$_{1-5}$-hydroxyalkylammonium, or ammonium based on amines derived from nitrogen-containing five- or six-membered saturated heterocycles, such as pyrrolidine, piperidine, morpholine or piperazine or their N-monoalkyl- or N,N-dialkyl-substituted products; wherein R2 and R3 are attached to the aromatic ring at any position;
k, m are, independently of each other, an integer from 1 to 3, preferably 1 or 2, most preferably 1;
water, and, optionally, a dispersing agent;
with the proviso that, if the aqueous preparation contains no dispersing agent and R1 is hydrogen, at least one of R2 and R3 is not hydrogen, preferably both R2 and R3 are not hydrogen.

A preferred proviso is that, if R1 is hydrogen, at least one of R2 and R3 is not hydrogen, preferably both R2 and R3 are not hydrogen.

Further, the present invention relates to the use of the aqueous preparation for dyeing or printing materials containing cellulose and/or polyamide, in particular a cellulose-containing material, preferably paper. In a preferred embodiment, the cellulose-containing material is a pulp or a sheet containing cellulosic material. The invention also relates to a process for dyeing or printing materials containing cellulose and/or polyamide, and a product or paper obtained by the process. Further preferred embodiments of the invention are described hereinafter and in the claims.

In a preferred embodiment, in the dyestuff of formula (1) R2 and R3, independently of each other, represent hydrogen, C$_{1-3}$-alkoxyl, or —SO$_3$M with M being defined as above, in particular R2 or R3 is methoxy, ethoxy, phenoxy, or —SO$_3$M, wherein M is ammonium mono-, di- tri- or tetra-substituted by C$_{1-4}$-alkanolamines, especially monoethanol-, diethanol- and/or triethanolamine. The groups R2 and R3 may be in o-, m- or p-position. Depending on the number of groups, either p-position or the other positions are preferred. If there are two R2 or R3 groups at the aromatic ring (k or m is 2), these are preferably in o- and m-position. In the most preferred embodiment, there is one R2 group and one R3 group at each aromatic ring (k, m is 1) and both are in p-position.

In a further preferred embodiment, in the dyestuff of formula (1) R1 represents hydrogen, CN, or CF$_3$.

Possible substituents of the aryl, phenyl, and/or alkyl residues for R1, R2 and R3, respectively, in the compound of formula (1) are C$_1$-C$_4$-alkyl, C$_1$-C$_4$-alkoxy, halogen, hydroxyl, amino, sulfonic, carboxylic, CN or nitro. Preferably, aryl, phenyl and/or alkyl are not substituted.

In a particularly preferred compound of formula (1), R1 is H, and R2 and R3 are both —SO$_3$M, with M being defined as above. Further preferred in this embodiment, k and m are 1, and R2 and R3 are both in p-position. In a further particularly preferred compound of formula (1), R1 is H, and R2 and R3 are both methoxy. Further preferred in this embodiment, k and m are 1, and R2 and R3 are both in p-position The dispersing agent can be any dispersing agent known from the state of the art, which is suitable for dispersing the compound of formula (1). In a preferred embodiment, the dispersing agent is an alkoxylated aryl compound, preferably an ethoxylated or propoxylated aryl compound, in particular a compound as described in EP 1 285 941 A1 or EP 1 184 402 A2. Preferred dispersing agents have the following formula (2):

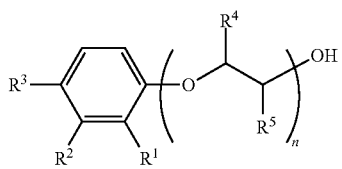

(2)

wherein $R^1$, $R^2$ and $R^3$ are, independently of each other, hydrogen, optionally substituted cyclohexyl or phenyl, wherein at least one of the residues $R^1$ to $R^3$ is not hydrogen, $R^4$ and $R^5$ are, independently of each other, methyl or hydrogen, and n is an integer from 21 to 40.

Possible substituents of the cyclohexyl or phenyl residues are $C_1$-$C_4$-alkyl, $C_1$-$C_4$-alkoxy, halogen, CN or nitro. Preferably, phenyl and/or cyclohexyl are not substituted. Preferably, in the compound of formula (2) n is an integer of 26 to 35, most preferably n=29 to 31. Further preferred, $R_3$ is phenyl. In another preferred embodiment, at least one of R1 to R3 is cyclohexyl. In the most preferred dispersing agent, $R_3$ is phenyl, $R_1$, $R_2$, $R_4$ and $R_5$ are hydrogen, and n is 30.

In another preferred embodiment, the dispersing agent is a polyalkylenepolyimine, in particular such a compound as described in EP 1 555 280 A2. Preferred dispersing agents are polyalkylenepolyimines having alkoxy units and anionic groups, especially those from the group consisting of —COO$^-$, —SO$_3^-$, —OSO$_3^-$, —PO$_3^{2-}$ and —P(OR)O$_2^-$, wherein R represents hydrogen or optionally substituted alkyl, cycloalkyl or aryl.

The aqueous preparation of the dyestuff of formula (1) contains preferably 0.01 to 50% by weight, more preferably 0.5 to 20% by weight, most preferably 1 to 10% by weight, in each case of compound of formula (1). Preferably, the aqueous preparation contains 0 to 10% by weight, more preferably 0.05 to 5% by weight, most preferably 0.1 to 2% by weight, in each case of dispersing agent. The remainder can be water. In an alternative embodiment, the aqueous preparation contains, in addition to the water, further common auxiliaries, such as biocides, UV absorbers, surfactants, urea, or caprolactam. The aqueous preparation contains one or more compounds of formula (1), e.g. 1, 2, or 3 formula (1) compounds, preferably one formula (1) compound. The aqueous preparation may also contain one or more other known dyes.

The aqueous preparation is a dispersion or solution, depending on the water solubility of the compound of formula (1). If the compound of formula (1) is not soluble in water, a dispersing agent is added. The aqueous preparation is prepared by dissolving or dispersing the formula (1) compound in water, optionally using the dispersing agent.

The compounds of formula (1) can be synthesized according to methods known in the art, for instance, as described in the literature by K. Suzuki et al., Chem. Eur. J. 2009, 15, p. 1096-1106. Compounds of formula (1) can be, for example, obtained from α-formylated furopyrrole and α-carboxylated furopyrrole in the presence of trifluoroacetic acid and trichlorophosphate with subsequent reaction with boron trifluoride in the presence of trifluoroacetic acid and triethylamine.

An exemplary general reaction scheme is:

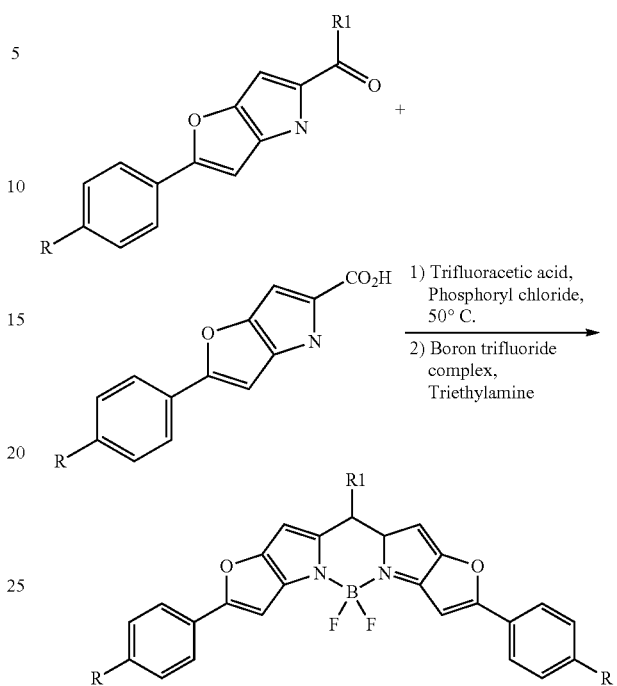

The aqueous preparation can be used for dyeing or printing materials, in particular materials containing cellulose and/or polyamide, preferably cellulose-containing material, in particular paper. In a preferred embodiment, the cellulose-containing material is a pulp or a sheet containing cellulosic material. Preferably, the aqueous preparation is used for dyeing a cellulose-containing material in the pulp, in a size press, and/or by a coating application. In particular, coating application means use of a coating composition or coating colour and/or coating equipment or apparatus. The pulp used may be any wood or plant fiber, e.g. bleached or unbleached, chemical, chemi-mechanical or mechanical pulp, or regenerated cellulosic material, or recycled paper fiber, or any combination thereof. The aforesaid uses can be applied singly or in a combination of two or more thereof. Further, the aqueous preparation can be used for printing paper, tissue, textile, such as cotton, wool. In addition, the aqueous preparation can be used in dyeing water-based coatings and plastics, such as polyamide. Further, it is also possible to use paper strips containing compounds of the present invention as test strips for labelling reactions. Furthermore, the aqueous preparation can be used for printing of materials, in particular materials containing cellulose and/or polyamide, preferably cellulose.

The invention also relates to a process for dyeing or printing materials containing cellulose and/or polyamide, preferably cellulose-containing material, in particular paper, wherein the material is brought into contact with an aqueous preparation as described above. Suitable materials for the process are the same as the materials described above with respect to the use of the aqueous preparation. Preferably, the contacting of the cellulose-containing material with the aqueous preparation is carried out in the pulp, in a size press, or by a coating application. In case of a coating application, preferably a coating composition or coating colour and/or coating equipment or apparatus is used.

The following Example illustrates the invention without limiting its scope. The Example demonstrates the synthesis of a compound of formula (1) and its use in an aqueous preparation for dyeing paper.

EXAMPLE

A compound of formula (1), wherein R2 and R3=OCH$_3$ and R1=H, is synthesized from 2-(4-methoxyphenyl)-4H-furo[3,2-b]pyrrole-5-carboxylic acid and 2-(4-methoxyphenyl)-4H-furo[3,2-b]pyrrole-5-carbaldehyde according to the general scheme given above and as described in K. Suzuki et al., Chem. Eur. J. 2009, 15, p. 1096-1106.

For production of the aqueous preparation, 200 mg of the above formula (1) compound (R2 and R3=OCH$_3$ and R1=H) and 10 mg of a dispersing agent are dissolved in 10 ml deionized water with intensive stirring until a green dispersion is obtained. The dispersing agent used is the reaction product of 1 mole 4-hydroxy biphenyl and 30 moles ethylene oxide according to EP 1 285 941 A1 or EP 1 184 402 A2, e.g. Example 1 thereof.

Dyeing Process:

7 parts by weight of chemically bleached pinewood sulfite cellulose and 3 parts by weight of chemically bleached birchwood sulfite cellulose are beaten with water in a mixer. 1 part by weight of the liquid dye preparation is added to this stuff followed by mixing for 20 minutes and producing handsheets from that. The obtained paper has a turquoise green color.

Thus, the present invention enables the production of paper with brilliant colors.

The invention claimed is:

1. An aqueous preparation comprising: a compound of formula (1),

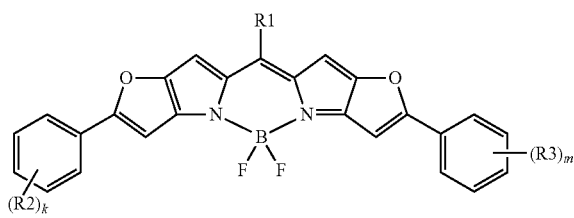

(1)

water, and
optionally, a dispersing agent,
wherein
R1 represents hydrogen, CN, CF$_3$, Br, Cl, I, optionally substituted aryl, or optionally substituted alkyl;
R2 and R3, independently of each other, represent hydrogen, C$_{1-5}$-alkyl, C$_{1-5}$-alkoxyl, optionally substituted aryl, optionally substituted phenyl, p-C$_{1-5}$-alkoxyphenyl, a di(C$_{1-5}$-alkyl)amino group, or —SO$_3$M, wherein M is mono-, di-, tri- or tetra-substituted ammonium substituted by C$_{1-5}$-alkyl and/or C$_{1-5}$-hydroxyalkyl;
R2 and R3 are attached to the aromatic ring at any position, wherein at least one of R2 or R3 is —SO$_3$M; and
k and m are, independently of each other, an integer from 1 to 3.

2. The aqueous preparation of claim 1, wherein R2 and R3, independently of each other, represent hydrogen, C$_{1-3}$-alkoxyl, or —SO$_3$M.

3. The aqueous preparation of claim 1, wherein R1 represents hydrogen, CN or CF$_3$.

4. The aqueous preparation of claim 1, wherein the compound of formula (1) contains one R2 group and one R3 group, each in p-position.

5. The aqueous preparation of claim 1, wherein R1 is hydrogen, and R2 and R3 both are —SO$_3$M.

6. The aqueous preparation of claim 1, wherein the dispersing agent is a compound of formula (2):

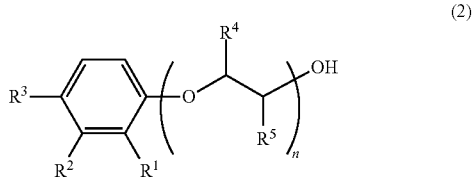

(2)

wherein
R$^1$, R$^2$ and R$^3$ are, independently of each other, hydrogen, optionally substituted cyclohexyl or phenyl;
at least one of the residues R$^1$ to R$^3$ is not hydrogen; R$^4$ and R$^5$ are, independently of each other, methyl or hydrogen; and
n is an integer from 21 to 40.

7. The aqueous preparation of claim 1, containing 0.01 to 50% by weight of the compound of formula (1), and 0 to 10% by weight of the dispersing agent.

8. A process for dyeing or printing materials containing cellulose and/or polyamide, wherein the material is brought into contact with an aqueous preparation as defined in claim 1.

9. The process of claim 8, wherein the cellulose-containing material is pulp or a sheet containing cellulosic material.

10. The process of claim 8, wherein the contacting of the cellulose-containing material is carried out in the pulp, in a size press, and/or by a coating application.

11. A paper or product obtainable by a process according to claim 8.

* * * * *